United States Patent

Wismer

Patent Number: 5,208,398
Date of Patent: May 4, 1993

[54] HF EXTRACTION OF R365 FROM R141B

[75] Inventor: John A. Wismer, Hamilton Square, N.J.

[73] Assignee: Elf Atochem N.A., Inc., Philadelphia, Pa.

[21] Appl. No.: 869,977

[22] Filed: Apr. 16, 1992

[51] Int. Cl.$^5$ ............................................. C07C 17/38
[52] U.S. Cl. .................................................... 570/177
[58] Field of Search ................................. 570/180, 177

[56] References Cited

U.S. PATENT DOCUMENTS

| | | | |
|---|---|---|---|
| 3,716,593 | 2/1973 | Hutson et al. | 570/177 |
| 3,947,558 | 3/1976 | van Eijl | 570/180 |
| 4,209,470 | 6/1980 | Lorquet | 570/180 |
| 5,099,081 | 3/1992 | Bolmer et al. | 570/180 |
| 5,099,082 | 3/1992 | Bolmer et al. | 570/180 |

Primary Examiner—Alan Siegel

[57] ABSTRACT

Separation of a mixture of R365 and R141b by liquid-liquid extraction with HF.

2 Claims, No Drawings

HF EXTRACTION OF R365 FROM R141B

FIELD OF THE INVENTION

The present invention relates to a method of separating a mixture of 1,1,1,3,3-pentafluorobutane ("R365") and 1,1-dichloro-1-fluoroethane ("R131b") by liquid-liquid extraction with hydrofluoric acid ("HF").

BACKGROUND OF THE INVENTION

R365, a solvent and precursor for other chemicals, is a by-product formed during the manufacture of R141b, a replacement for trichlorofluoromethane as a blowing agent, and 1-chloro-1,1-difluoroethane ("R142b"), a key intermediate in the production of polyvinylidene fluoride, by the liquid phase hydrofluorination of 1,1,1-trichloroethane, as described, for example, in EP 297,947. While R365 is generated in small amounts, typically about 0.5 weight percent based on the amount of R141b product, R365 and R141b have similar boiling points (40C and 32C, respectively) and form an azeotrope having a composition of about 19 mol % R365 and 81 mol % R141b, making separation by conventional distillation means extremely difficult.

While liquid-liquid solvent extraction techniques have been disclosed, as in U.S. Pat. No. 4,031,148, the introduction of substances foreign to the manufacturing process is undesirable since they would require extensive post-extraction purification and solvent recovery.

Thus, what is needed is a method for the removal of R365 from R141b which is efficient and, preferably, compatible with the manufacturing process.

SUMMARY OF THE INVENTION

A method is provided for separation of R365 from a mixture containing R365 and R141b which method comprises liquid-liquid extraction on the mixture in the presence of HF. More specifically, the process comprises contacting a mixture containing R365 and R141b with HF such that the HF extracts R365 from the mixture and forms a separate phase therefrom, then separating the resultant phases of R365-rich HF and the R365/R141b mixture, which mixture now has a correspondingly reduced concentration of R365. The R365/R141b feed mixture may also contain R142b.

DETAILED DESCRIPTION OF THE INVENTION

It has now been found that efficient separation of R365 and R141b can be achieved via liquid-liquid extraction with HF, thus avoiding the need for introducing foreign substances into the manufacturing process for producing R141b and/or R141b/R142b mixtures from 1,1,1-trichloroethane and HF.

The separation can be carried out in a liquid-liquid extractor, the configuration of which can be any of a number of designs known in the art, such as a rotating disk column, a pulse column, or even a mixer/settler system. In a conventional vertical column design the less dense HF stream is fed at the column bottom and the more dense HCFC stream of R365, R141b, and, optionally, R142b, is fed at the top. Regardless of design, the extractor should provide for countercurrent flow of the HF and HCFC feed streams, intimate mixing of the HF and HCFC phases, and enough theoretical stages to effect the desired separation. The exact number of such stages depends on process conditions, feed quality, specified product quality, and the like. With the vertical column, the effluent from the column bottom will be an HCFC-rich phase which contains some HF and which is rich in R141b (and R142b, if present in the feed) and lean in R365 relative to the feed, while the effluent from the top will be an HF-rich phase containing some HCFC which is now rich in R365 and lean in R141b (and R142b) relative to the feed.

Since HF is the extraction agent, this separation system can easily be integrated into the manufacturing system. Thus, the HF-rich effluent can be recycled to the reactor for use in the manufacturing operation or the HF can be recovered from this effluent via distillation and reused in the extraction system.

The extraction is generally operated at a temperature which is anywhere from about −40° C. to about to about +20° C. Temperatures of +20° C. and below assure that there is no significant reaction of HF with the 141b and prevent the system from becoming too miscible in the presence of some R142b, which is more soluble in HF than R141b. Temperatures of above −20° C. provide enough miscibility to affect a reasonable extraction efficiency.

The weight ratios of the feed streams are generally such that the ratio of HF to R141b is from about 0.05:1 to 5:1. On either side of these ratios the extraction system tends to become relatively ineffective since it becomes too close to the one-phase region. The preferred ratios are between 0.2:1 and 2:1. The appropriate feed ratio is a complex function of a number of variables, including temperature, number of equilibrium stages, purity of the R141b feed, and purity of the R141b effluent. In general, for example, the more the equilibrium stages for a given degree of separation, the less the required HF/R141b ratio. The lower the temperature, the lower the system miscibility, and hence the higher the permissible HF/R141b ratio. The higher the R142b content of the feed, the greater the system miscibility and the lower the optimal HF/R141b ratio. The higher the HF ratio, the higher the degree of separation between R365 and R141b, other variables being equal.

To demonstrate the invention the following experiments were done and results evaluated using a separation factor which is defined as the ratio of R365 to R141b in the resulting HF-rich phase divided by the ratio of R365 to R141b in the resulting HCFC phase. All component amounts are in weight percent.

EXAMPLE 1

R365, R141b, and HF were mixed and then allowed to settle into two phases at 20° C., with the following results:

|       | Charge Comp. | HF Phase | HCFC Phase |
|-------|--------------|----------|------------|
| HF    | 42.19        | 80.98    | 1.88       |
| R365  | 3.36         | 2.61     | 4.45       |
| R141b | 54.45        | 16.41    | 93.67      |

The separation factor is 3.35.

EXAMPLE 2

Example 1 was modified to measure the effect of higher R365 concentrations in the HCFC feed.

|       | Charge Comp. | HF Phase | HCFC Phase |
|-------|--------------|----------|------------|
| HF    | 34.83        | 60.18    | 6.08       |
| R365  | 27.02        | 20.60    | 32.85      |

| | Charge Comp. | HF Phase | HCFC Phase |
|---|---|---|---|
| R141b | 38.15 | 19.22 | 61.07 |

The separation factor is 1.99.

EXAMPLE 3

Example 1 was modified to measure the effect of R142b on the separation factor.

| | Charge Comp. | HF Phase | HCFC Phase |
|---|---|---|---|
| HF | 37.53 | 64.41 | 4.05 |
| R365 | 3.42 | 2.85 | 4.77 |
| R141b | 31.91 | 14.07 | 55.71 |
| R142b | 27.14 | 18.67 | 35.47 |

The separation factor is 2.37.

EXAMPLE 4

Example 3 was modified to measure the effect of temperature. Thus, this example was conducted at 0° C. as opposed to 20° C. in the previous tests.

| | Charge Comp. | HF Phase | HCFC Phase |
|---|---|---|---|
| HF | 41.38 | 74.19 | 2.06 |
| R365 | 3.21 | 2.33 | 5.02 |
| R141b | 29.04 | 8.91 | 54.47 |
| R142b | 26.37 | 14.57 | 38.45 |

The separation factor is 2.84.

What is claimed is:

1. A method of separating a mixture containing 1,1,1,3,3-pentafluorobutane and 1,1-dichloro-1-fluoroethane comprising liquid-liquid extraction of said mixture with hydrofluoric acid.

2. A method as in claim 1 wherein the mixture also contains 1-chloro-1,1-difluoroethane.

* * * * *